US010158956B2

(12) United States Patent
Theill

(10) Patent No.: US 10,158,956 B2
(45) Date of Patent: Dec. 18, 2018

(54) METHOD OF FITTING A HEARING AID SYSTEM, A HEARING AID FITTING SYSTEM AND A COMPUTERIZED DEVICE

(71) Applicant: Widex A/S, Lynge (DK)

(72) Inventor: Jesper Theill, Lynge (DK)

(73) Assignee: Widex A/S, Lynge (DK)

( * ) Notice: Subject to any disclaimer, the term of this patent is extended or adjusted under 35 U.S.C. 154(b) by 39 days.

(21) Appl. No.: 15/428,219

(22) Filed: Feb. 9, 2017

(65) Prior Publication Data

US 2017/0238106 A1    Aug. 17, 2017

(30) Foreign Application Priority Data

Feb. 11, 2016 (DK) ................. 2016 00088

(51) Int. Cl.
*A61B 5/00* (2006.01)
*H04R 25/00* (2006.01)
*A61B 5/12* (2006.01)

(52) U.S. Cl.
CPC ............ *H04R 25/70* (2013.01); *A61B 5/123* (2013.01); *A61B 5/7475* (2013.01); *H04R 25/35* (2013.01); *H04R 2225/43* (2013.01)

(58) Field of Classification Search
CPC combination set(s) only.
See application file for complete search history.

(56) References Cited

U.S. PATENT DOCUMENTS

| 2001/0049480 A1* | 12/2001 | John ................. A61B 5/04845 600/559 |
| 2002/0068986 A1 | 6/2002 | Mouline |
| 2011/0004468 A1 | 1/2011 | Fusakawa et al. |
| 2012/0132004 A1 | 5/2012 | Ito |

FOREIGN PATENT DOCUMENTS

| WO | 01/26272 A2 | 4/2001 |
| WO | 2016/046079 A1 | 3/2016 |

OTHER PUBLICATIONS

Search Report for PA 2016 00088, dated May 24, 2016.

* cited by examiner

*Primary Examiner* — Amir Etesam
(74) *Attorney, Agent, or Firm* — Sughrue Mion, PLLC

(57) ABSTRACT

A method (100) of fitting a hearing aid system comprising identification of an auditory neuro-synaptopathy of a person based on the sensitivity of the person to temporal masking, a hearing aid fitting system, a computerized device (200, 300), a server (302) hosting a web service and a computer-readable storage medium having computer-executable instructions, which when executed carry out said method.

12 Claims, 2 Drawing Sheets

METHOD OF FITTING A HEARING AID SYSTEM, A HEARING AID FITTING SYSTEM AND A COMPUTERIZED DEVICE

The present invention relates to a method of fitting a hearing aid system and a hearing aid fitting system. The present invention also relates to a computerized device configured to identify an auditory neuro-synaptopathy of a person. The present invention furthermore relates to a computer-readable storage medium having computer-executable instructions, which when executed carry out a method of identifying an auditory neuro-synaptopathy of a person. The invention further relates to a server hosting a web service.

BACKGROUND OF THE INVENTION

Generally a hearing aid system according to the invention is understood as meaning any system which provides an output signal that can be perceived as an acoustic signal by a user or contributes to providing such an output signal, and which has means which are used to compensate for an individual hearing deficiency of the user or contribute to compensating for the hearing deficiency of the user. These systems may comprise hearing aids which can be worn on the body or on the head, in particular on or in the ear, and can be fully or partially implanted. However, some devices whose main aim is not to compensate for a hearing deficiency may also be regarded as hearing aid systems, for example consumer electronic devices (televisions, hi-fi systems, mobile phones, MP3 players etc.), provided they have, however, measures for compensating for an individual hearing deficiency.

Within the present context a hearing aid may be understood as a small, battery-powered, microelectronic device designed to be worn behind or in the human ear by a hearing-impaired user.

Prior to use, the hearing aid is adjusted by a hearing aid fitter according to a prescription. The prescription is conventionally based on a hearing test that measures the hearing threshold, resulting in a so-called audiogram, of the performance of the hearing-impaired user's unaided hearing. The prescription may be developed to reach a setting where the hearing aid will alleviate a hearing deficiency by amplifying sound at frequencies in those parts of the audible frequency range where the user suffers a hearing deficit in the form of an elevated hearing threshold.

A hearing aid comprises one or more microphones, a battery, a microelectronic circuit comprising a signal processor, and an acoustic output transducer. The signal processor is preferably a digital signal processor. The hearing aid is enclosed in a casing suitable for fitting behind or in a human ear. For this type of traditional hearing aids the mechanical design has developed into a number of general categories. As the name suggests, Behind-The-Ear (BTE) hearing aids are worn behind the ear. To be more precise, an electronics unit comprising a housing containing the major electronics parts thereof is worn behind the ear and an earpiece for emitting sound to the hearing aid user is worn in the ear, e.g. in the concha or the ear canal. In a traditional BTE hearing aid, a sound tube is used to convey sound from the output transducer, which in hearing aid terminology is normally referred to as the receiver, located in the housing of the electronics unit and to the ear canal. In some modern types of hearing aids a conducting member comprising electrical conductors conveys an electric signal from the housing and to a receiver placed in the earpiece in the ear. Such hearing aids are commonly referred to as Receiver-In-The-Ear (RITE) hearing aids. In a specific type of RITE hearing aids the receiver is placed inside the ear canal. This category is sometimes referred to as Receiver-In-Canal (RIC) hearing aids. In-The-Ear (ITE) hearing aids are designed for arrangement in the ear, normally in the funnel-shaped outer part of the ear canal. In a specific type of ITE hearing aids the hearing aid is placed substantially inside the ear canal. This category is sometimes referred to as Completely-In-Canal (CIC) hearing aids. This type of hearing aid requires an especially compact design in order to allow it to be arranged in the ear canal, while accommodating the components necessary for operation of the hearing aid.

Some hearing aid systems do not comprise a traditional loudspeaker as output transducer. Examples of hearing aid systems that do not comprise a traditional loudspeaker are cochlear implants, implantable middle ear hearing devices (IMEHD) and bone-anchored hearing aids (BAHA). Within the present context a hearing aid system may comprise a single hearing aid (a so called monaural hearing aid system) or comprise two hearing aids, one for each ear of the hearing aid user (a so called binaural hearing aid system). Furthermore the hearing aid system may comprise an external device, such as a smart phone having software applications adapted to interact with other devices of the hearing aid system, or the external device alone may function as a hearing aid system. Thus within the present context the term "hearing aid system device" may denote a traditional hearing aid or an external device.

It is well known for persons skilled in the art of hearing aid systems that some hearing aid system users are not satisfied with results of conventional hearing-aid fitting that primarily is based on measuring an elevated hearing threshold.

A subgroup of potential hearing aid users is assumed to suffer from an auditory neuro-synaptopathy due to aging or ototoxic drug exposure or noise trauma. This type of hearing deficit may also be denoted an auditory neurodegeneration if preferring a more general term. Auditory neuro-synaptopathy is a dysfunction in the synapses that transmits hearing information from e.g. the inner hair cells of the cochlea and to nerve-fibres that carry the hearing information further on to the processing parts of the brain. A plurality of synapses are required to be activated in order to provide that a nerve-fibre is activated and transmits the hearing information.

Measurement of the hearing threshold cannot generally be used to diagnose this type of hearing deficiency. Many hearing aid fitters may therefore be hesitant to suggest or apply potentially beneficial sound-processing features specifically adapted to relieve an auditory neuro-synaptopathy, unless a hearing aid fitting system capable of detecting an auditory neuro-synaptopathy is available.

It is therefore a feature of the present invention to provide a hearing aid fitting system or some other computerized device capable of detecting an auditory neuro-synaptopathy.

Such a measurement may also detect hearing deficiencies for those persons that complain about a problem with understanding speech in noise, but do not reveal an elevated hearing threshold (that may also be denoted reduced pure-tone sensitivity). Today, these persons are not prescribed hearing-aid system treatment and are therefore left to cope with their hearing deficit.

According to another aspect it is a feature of the present invention to suggest a method of fitting a hearing aid system that comprises detection of an auditory neuro-synaptopathy in a manner that is time-efficient and easy to execute such that it may be suitable for implementation as part of a standard hearing aid fitting procedure.

It is another feature of the present invention to provide a hearing aid fitting system capable of suggesting and providing features specifically directed at relieving an auditory neuro-synaptopathy.

SUMMARY OF THE INVENTION

The invention, in a first aspect, provides a method of fitting a hearing aid system according to claim 1.

The invention, in a second aspect, provides a computer-readable storage medium having computer-executable instructions according to claim 11.

The invention, in a third aspect, provides a hearing aid fitting system according to claim 12.

The invention in a fourth aspect, provides a computerized device according to claim 13.

The invention in a fifth aspect, provides a server hosting a web service according to claim 14.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects, all without departing from the invention. Accordingly, the drawings and descriptions will be regarded as illustrative in nature and not as restrictive. In the drawings.

DETAILED DESCRIPTION

Figure 1:
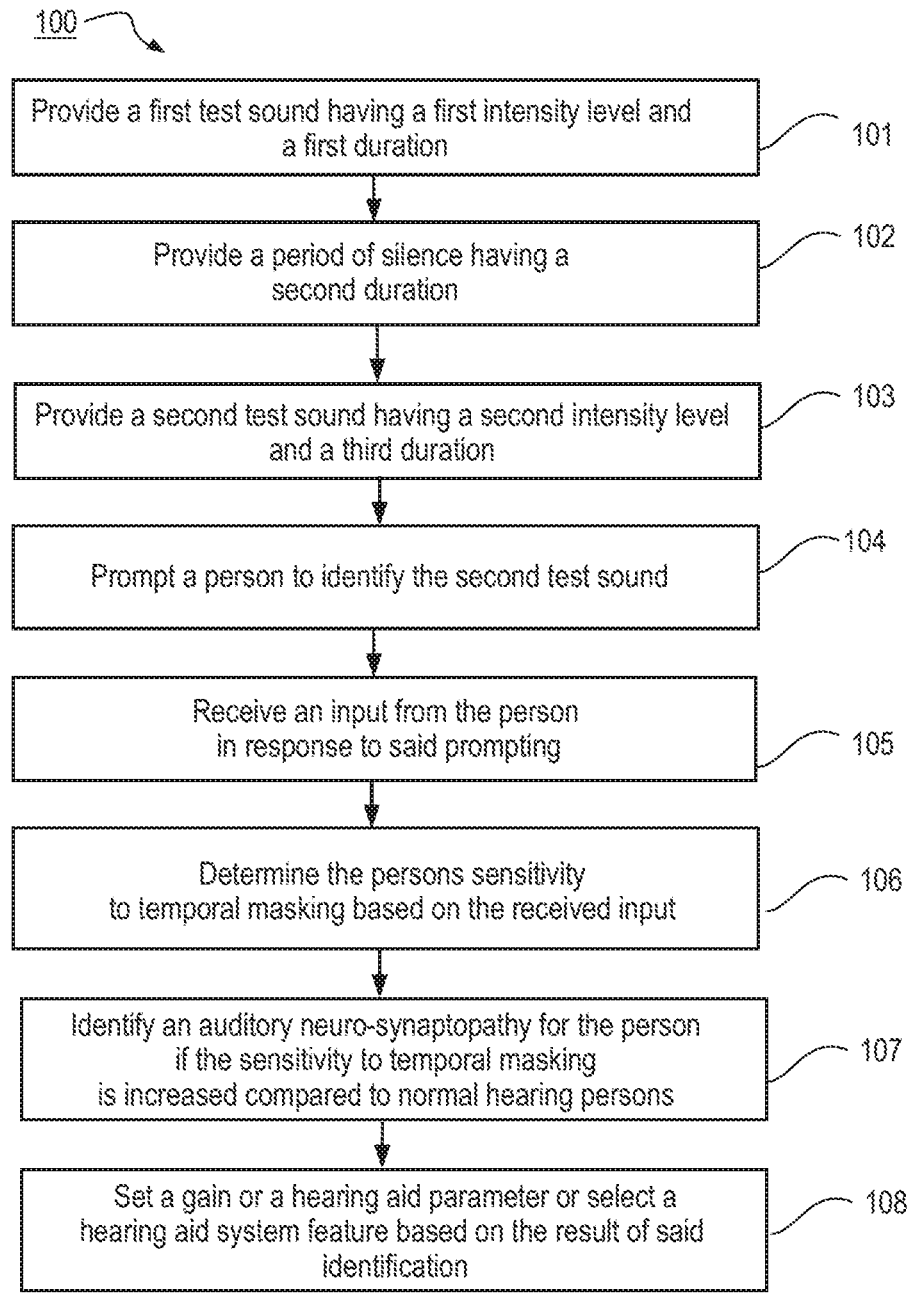
FIG. 1 illustrates highly schematically a method of fitting a hearing aid system according to an embodiment of the invention.

Within the present context the term software application may be construed to comprise a program storage for storing an executable program, and a processor for executing said program. However, the term software application may also be construed to mean a non-transitory computer readable medium carrying instructions that may be executed by a computer.

The inventors have realized that people with auditory neuro-synaptopathy may be particularly sensitive to temporal masking. Temporal masking (which may also be denoted non-simultaneous masking) is the characteristic of the auditory system where sounds are hidden due to maskers that have just disappeared. The effect of masking after a strong sound is called post-masking, and can be in effect up to 200 milliseconds.

It is presently believed that people with auditory neuro-synaptopathy may be more sensitive to temporal masking due to the auditory nerve synapses, which transmits hearing signals from the inner hair cells and to an auditory nerve-fibre and on to other parts of the brain for further processing, exhibiting different characteristics dependent on whether the corresponding auditory nerve-fibre is adapted to respond to respectively low, medium or high sound pressure levels. In the following an auditory nerve-fibre may be construed to comprise both the synapses and the corresponding nerve-fibre, and in the following an auditory nerve-fibre may also simply be denoted a nerve-fibre.

The auditory nerve-fibres that respond to low sound pressure levels are typically denoted high-spontaneous rate (HSR) nerve-fibres and are characterized in that their temporal response is relatively slow. As opposed hereto the auditory nerve-fibres that respond to the medium and high sound pressure levels typically exhibit a temporal response that is relatively faster. These nerve-fibres are typically denoted respectively medium-spontaneous rate (MSR) nerve-fibres and low-spontaneous rate (LSR) nerve-fibres. For normal hearing persons the low sound pressure levels that the HSR nerve-fibres primarily respond to are in the range between say 0-40 dB SPL, the medium sound pressure levels that the MSR nerve-fibres primarily respond to are in the range between say 20-100 dB SPL, and the high sound pressure levels that the LSR nerve-fibres primarily respond to are in the range between say 40-120 dB SPL. For persons suffering from a hearing deficit that results in an elevated hearing threshold the HSR nerve-fibres will primarily respond to sound pressure levels in the range between the hearing threshold (i.e. 0 dB SL) and 40 dB above the hearing threshold (i.e. 40 dB SL), the medium sound pressure levels that the MSR nerve-fibres primarily respond to are in the range between say 20-100 dB SL and the high sound pressure levels that the LSR nerve-fibres primarily respond to are in the range between say 40-120 dB SL. However, it is noted that for persons suffering from a more complex hearing deficiency, such as an outer hair cell loss, the above ranges may be different especially for the sound pressure levels that the MSR and LSR nerve-fibres primarily respond to.

The MSR and LSR nerve-fibres that respond to the medium and high sound pressure levels are characterized in that they, as opposed to the HSR nerves-fibres that primarily respond to low sound pressure levels, comprise two different types of synapses, wherein the second synapse type that is generally not part of the HSR nerve-fibres differs from the first type in that the second synapse type is faster, but also less robust against damage from e.g. ototoxic drug use or excessive sound exposure. Thus the HSR nerve-fibres, which primarily comprise nerve-fibres of the first type, are therefore expected to be slower but also more robust than the MSR and LSR nerve-fibres.

Assuming that the synapses of the second type have been damaged to the extent that they do not function properly anymore, which may very well be the case because of the vulnerability of this type of synapses, then this deficit will not impact the hearing threshold. However, this type of hearing deficit will have an impact on the sensitivity to temporal masking for the relatively high sound pressure levels that the MSR nerve-fibres and LSR nerve-fibres respond to.

The present invention therefore suggests a test based on the ability of a person to deal with temporal masking (i.e. the sensitivity of said person to temporal masking) in order to diagnose an auditory neurodegeneration such as an auditory neuro-synaptopathy.

The hearing aid fitting systems and computerized devices according to the present invention can therefore be used to identify persons suffering from auditory neuro-synaptopathy and hereby provide information of the hearing deficit beyond the conventional audiogram.

Additionally the disclosed methods of hearing aid fitting are advantageous in that the identification and quantification of an auditory neuro-synaptopathy may be used to prescribe and fit (which in the following may also be denoted to program) alternative methods of operating hearing aid systems, e.g. more aggressive noise-reduction algorithms, whereby persons suffering from this hearing deficit may achieve greater benefit from wearing a hearing aid system.

Reference is first made to FIG. 1, which illustrates highly schematically a method 100 of fitting a hearing aid system according to an embodiment of the invention. The method comprises the steps of:

providing, in a first step 101, a first test sound having a first intensity level and a first duration;

providing, in a second step 102, a period of silence, immediately after said first test sound, wherein the period of silence has a second duration;

providing, in a third step 103, a second test sound, immediately after said period of silence, wherein the second test sound has a second intensity level and a third duration;

prompting, in a fourth step 104, a person to identify the second test sound;

receiving, in a fifth step 105, an input from the person in response to said prompting;

determining, in a sixth step 106, the person's sensitivity to temporal masking based on the input from the person;

identifying, in a seventh step 107, an auditory neuro-synaptopathy for the person if the sensitivity to temporal masking is increased compared to that of normal hearing persons; and setting, in an eighth step 108, a gain or a hearing aid parameter or selecting a hearing aid feature based on the result of said identification.

Pure tones are used as the first and second test sounds. However, in variations other narrowband test sounds may be used, such as warble tones or narrow-band noise, wherein narrowband may be construed to mean that the frequency content of the test sound primarily is within one hearing aid system frequency band or alternatively within one of the so called critical bands, that may also be denoted auditory filters or Bark bands.

In other variations the second test sound may be slightly frequency shifted relative to the first test sound in order to improve the detectability for the test person. Preferably the frequency shift is less than 10% or even less than 5% of the centre frequency of the first test sound.

The intensity level of the first test sound (that in the following may also simply be denoted first intensity level) is set to 50 dB SL or selected from a range between 20 dB SL and 80 dB SL. This range ensures that a sufficient activation of the MSR and LSR nerve-fibres is provided. Additionally this range of first intensity levels provides a reasonable compromise between the limited dynamic range of input intensity levels that may be available for people suffering from an elevated hearing threshold and the desire to optimize the precision of the assessment of the sensitivity to temporal masking by activating as many of MSR and LSR nerve-fibres as possible. It is a specific advantage to select the first intensity level based on the dB SL scale, since this allows the sensitivity to temporal masking between normal hearing persons and people with an elevated hearing threshold to be compared in a simple and direct manner.

The duration of the first test sound is set to be 200 milliseconds or selected from a range between 100 milliseconds and 1 second. This range provides a compromise between the desire to have a test method that is not too lengthy while on the other hand ensuring that a sufficient amount of nerve-fibres have been activated in order to optimize the precision of the assessment of the sensitivity to temporal masking, because the inventor has found that the precision may suffer if a higher intensity first test sound of shorter duration is applied, because the reproducibility, of the amount of activated nerve-fibres, as a result of the first test sound, starts to decrease if the duration of the first test sound becomes too short.

The intensity level of the second test sound (that in the following may also simply be denoted second intensity level) is set to be 20 dB lower than the first intensity level, or the second intensity level may be selected from a range between 10 dB and 40 dB lower than the first intensity level. It is a specific advantage to select the second intensity level relative to the first intensity level because this provides that the determined sensitivity to temporal masking between normal hearing persons and people with a conductive, sensorineural or mixed hearing loss with an elevated hearing threshold is as independent as possible of the selected intensity level of the first test sound. In a specific variation the difference, between the first and second intensity levels, is increased as the first intensity level is increased because a larger difference generally facilitates the determination of the sensitivity to temporal masking. However, a too small value of the second intensity level, say in the range below 10 dB SL may adversely affect the ability to determine the sensitivity to temporal masking.

The duration of the second test sound (that in the following may also simply be denoted the third duration) is set to be 10 milliseconds or selected from a range between 5 milliseconds and 50 milliseconds. This range provides that the duration of the second test sound is sufficiently long such that it can be perceived by the test person while on the other hand generally avoiding that the duration of the second test sound becomes so long that even people suffering from increased sensitivity to temporal masking will be able to perceive the second test sound and hereby making it impossible to detect a difference in the sensitivity to temporal masking.

The duration of the period of silence (that in the following may also simply be denoted the second duration) between the two test sounds is varied iteratively until the second duration that makes the second test sound just noticeable has been determined. According to the present embodiment the duration of the period of silence is initially set to 20 milliseconds and may subsequently be varied in the range between say 5 milliseconds and 200 milliseconds. The upper limit of this range is selected to correspond to the generally accepted upper limited for the duration of temporal masking and the lower limit is selected in order to provide a sufficiently long period of silence such that the test person may distinguish the second test sound from the first test sound.

According to the present embodiment the duration of the period of silence (i.e. the second duration) is iteratively varied, depending on the responses of the test person, until the duration of the period of silence that makes the second test sound just noticeable has been determined, and in case the determined just noticeable second duration is significantly longer than a corresponding value for normal hearing persons, then an auditory neurodegeneration is identified.

In a variation the second duration that makes the second test sound just noticeable is determined for a plurality of first intensity levels, and in case the second duration that makes the second test sound just noticeable does not decrease for some high value of the first intensity levels relative to some lower value of the first intensity level, then an auditory neurodegeneration is identified, because this case reflects that the fast MSR nerve-fibres or the fast LSR nerve-fibres or both of them have been damaged in some way and consequently don't provide the expected reduction in sensitivity to temporal masking. The high value of the first test sound intensity level is construed to mean that the first test sound intensity level is sufficiently high to activate the MSR and/or LSR nerve-fibres, which is the case for first intensity levels above 50 dB SL, wherefrom it follows that the lower value of the first intensity level is selected from the range between 10-50 dB SL.

According to a more specific variation the first intensity level is initially set to 40 dB SL and then increased in steps of 10 dB until approaching the uncomfortable level of the test person.

According to a second embodiment an auditory neuro-synaptopathy is identified based on a determination of the level difference between the first and the second intensity levels that makes the second test sound just noticeable. According to one specific variation the first intensity level as well as the first, second and third durations are given values corresponding to the first embodiment, and the second intensity level is varied iteratively until the lowest intensity level that makes the second test sound just noticeable has been determined. Thus according to this specific variation the duration of the period of silence is set to 20 milliseconds, which will make temporal masking important with respect to the ability of a person to detect the second test sound because the refractory period of the nerve-fibres (or more precisely the slow synapses of the nerve-fibres) is typically in the range of 200 milliseconds. In further variations the duration of the period of silence is selected from a range between 10 and 50 milliseconds.

According to the second embodiment an auditory neuro-synaptopathy is identified in case the determined level difference, between the first and the second intensity level, that makes the second test sound just noticeable is significantly higher than the corresponding value for normal hearing persons.

In a more specific variation the level difference, between the first and the second intensity level, that makes the second test sound just noticeable is determined for a plurality of first intensity levels, and in case the determined level difference does not increase for some high value of the first intensity level, relative to a determined level difference for some lower value of the first intensity level, then an auditory neurodegeneration is identified, because this case reflects that the fast MSR nerve-fibres or the fast LSR nerve-fibres or both of them have been damaged in some way and consequently don't enable the person to take advantage of the reduced sensitivity to temporal masking that the fast nerve-fibres provide if functioning correctly. The high value of the first test sound intensity level is construed to mean that the first test sound intensity level is sufficiently high to activate the MSR and/or LSR nerve-fibres, which is the case for first intensity levels above 40 dB SL, wherefrom it follows that the lower value of the first intensity level is selected from the range between 10-40 dB SL.

According to further variations of the disclosed embodiments the method is carried out with a plurality of test tones with different frequency content in order to characterize the frequency dependence of a possible auditory neuro-synaptopathy. According to a more specific embodiment the method is carried out with a plurality of test tones that each represent a hearing aid frequency band.

Figure 2:
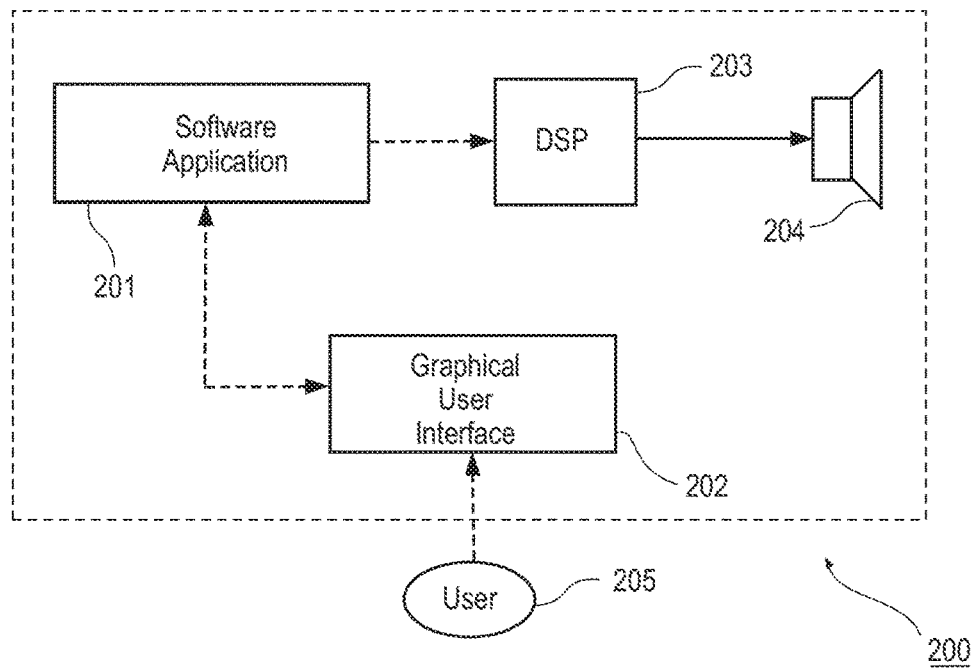
FIG. 2 illustrates highly schematically a computerized device according to an embodiment of the invention.

Reference is now made to FIG. 2, which illustrates highly schematically a computerized device 200 according to an embodiment of the invention. The computerized device 200 comprises a software application 201, a graphical user interface 202, a digital signal processor (DSP) 203 and an electro-acoustical output transducer 204.

FIG. 2 illustrates how a person 205 through the graphical user interface 202 may communicate interactively with the computerized device 200 in a manner controlled by the software application 201. The software application 201 is furthermore adapted to interact with the DSP 203 such that the electro-acoustical transducer 204 can be used to provide a desired acoustical test signal.

In correspondence with the first embodiment according to FIG. 1 the computerized device 200 is adapted to provide a first test sound at a first intensity level and a second test sound at a second intensity level, using the electro-acoustical output transducer 204, wherein the first test and second test sounds are separated by a period of silence of a certain duration.

Furthermore the computerized device 200 is adapted to prompt a person to respond each time the second test sound is detected, which may not be the case if the duration of the period of silence between the first and second test sounds is so short that the second test sound is masked by the first test sound, or the second test sound may not be detected if the second intensity level is not large enough relative to the first intensity level due to partial masking by the first test sound. The computerized device 200 is also adapted to receive, through the graphical user interface 202, an input from the person in response to said prompting, wherein said input represents the person's sensitivity to temporal masking because a positive detection of the second test sound means that the second test sound has not been temporally masked by the first test sound.

The shorter the period of silence can be while still allowing the second test sound to be detected, the lower the persons sensitivity to temporal masking. Further, the higher the level difference between the first and the second test sounds can be while still allowing the second test sound to be detected, the lower the persons sensitivity to temporal masking.

Therefore the computerized device 200 is adapted to vary up and down the duration of the period of silence between the first and second test sound, based on the response from the person, until the second test sound is perceived as just noticeable by the person. Additionally or alternatively the computerized device 200 may be adapted to vary up and down the second intensity level, based on the response from the person, until the second test sound is perceived as just noticeable by the person.

Finally the computerized device 200 is adapted to identify an auditory neuro-synaptopathy for the person if the sensitivity to temporal masking is not reduced relative to normal hearing persons. Additionally or alternatively the computerized device 200 may be adapted to identify an auditory neuro-synaptopathy for the person if the sensitivity to temporal masking for some high value of the first test sound intensity level is not reduced relative to the sensitivity to temporal masking at some relatively lower value of the first test sound intensity, wherein the high value of the first test sound intensity level is sufficiently high to activate the MSR and/or LSR nerve-fibres. Wherein the high value of the first test sound intensity level therefore is construed to mean that the first test sound intensity level is sufficiently high to activate the MSR and/or LSR nerve-fibres, which is the case for first intensity levels above 40 dB SL, wherefrom it follows that the lower value of the first intensity level is selected from the range between 5-40 dB SL.

In a specific variation the identification of an auditory neuro-synaptopathy may be used as input to a hearing aid fitting system, whereby alternative processing features directed specifically at relieving an auditory neuro-synaptopathy may be selected.

In a variation the computerized device 200 is adapted to identify an auditory neuro-synaptopathy if the duration of the period of silence between the first and second test sounds that makes the second test sound just noticeable is longer than a first threshold that is in the range between say 5 and 50 milliseconds.

In another variation the computerized device 200 is adapted to identify an auditory neuro-synaptopathy if the level difference, between the first intensity level and the second intensity level, that makes the second test sound just noticeable, is larger than a first threshold that is in the range between say 5 dB and 20 dB.

However, as will be clear from the preceding disclosure, the other parameters determining the applied test sounds also need to be considered in order to find an optimum setting for the test.

In a further variation the magnitude of the duration of the period of silence between the first and second test sounds that makes the second test sound just noticeable may be used as input to a hearing aid fitting system, whereby parameters of alternative processing features directed specifically at relieving an auditory neuro-synaptopathy may be set dependent on the severity of the auditory degeneration.

In further variations the computerized device 200 is adapted to be part of a conventional hearing aid fitting system, wherein the person to be tested is exposed to the test sounds from loudspeakers controlled by the computerized device and wherein the person responds by signaling his response to a hearing care professional (who may also be denoted a hearing aid fitter) who subsequently inputs the responses to the computerized device. In a more specific variation the computerized device controls at least one hearing aid worn by the person, whereby the test sounds can be provided by the hearing aids.

Figure 3:
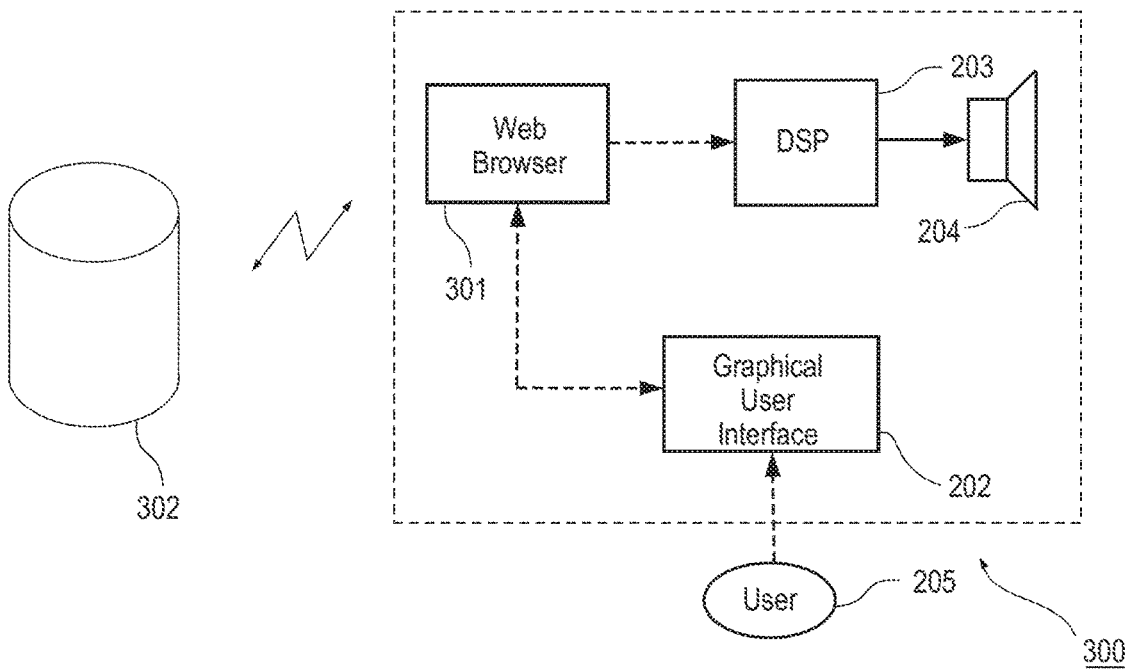
FIG. 3 illustrates highly schematically a computerized device and an external server according to an embodiment of the invention.

Reference is now made to FIG. 3, which illustrates highly schematically a computerized device 300 and an external server 302 according to an embodiment of the invention. The computerized device 300 comprises basically the same elements as the computerized device 200 from the embodiment of FIG. 2, except in so far that the functionality, which in the embodiment of FIG. 2 is provided by the software application 201, in the embodiment of FIG. 3 is provided by a web service that is hosted on the external server 302 and may be accessed using the web browser 301.

In variations of the FIGS. 2 and 3 embodiments the computerized device may be a smart phone, a tablet computer, a portable personal computer or a stationary personal computer. According to the embodiments of FIG. 2 and FIG. 3 the electro-acoustical transducer 204 is a traditional loudspeaker. However, the loudspeaker provides the acoustical test signal to both ears simultaneously, which may be less advantageous in some cases, e.g. if the person only has a hearing deficit in one ear. In variations the software application is therefore set up to provide an acoustical test signal that is selectively provided to either the left ear or the right ear using a set of standard headphones, earphones or even hearing aids connected to the computerized device.

It is a specific advantage of the present invention that it provides a quantitative measure of the auditory neuro-synaptopathy, such that the quantitative measure may be used to select the most appropriate processing for the person. As one example a person requiring a very long period of silence between a first and a second test sound in order to avoid temporal masking of the subsequent second test sound, which indicates a serious auditory neuro-synaptopathy, may benefit from more aggressive noise reduction algorithms or alternative processing schemes (which may also be denoted hearing aid features) directed at relieving the amount of sound that the auditory nerves are exposed to. Examples of such alternative hearing aid features comprise frequency contrast enhancement and interleaved frequency band processing.

The method of frequency contrast enhancement in a hearing aid system may be described by the steps of:

providing an electrical input signal representing an acoustical signal from an input transducer of the hearing aid system;

splitting the input signal into a first plurality of frequency bands;

determining a measure of the signal variability for each band of a second plurality of frequency bands;

determining a threshold level based on the determined measures of the signal variability for each band of the second plurality of frequency bands;

applying a first gain to a frequency band based on an evaluation of the determined measure of the signal variability for said frequency band relative to the threshold level;

combining the first plurality of frequency bands into an electrical output signal; and using the electrical output signal for driving an output transducer of the hearing aid system.

The method of interleaved frequency band processing in a hearing aid system may be described by the steps of:

providing an electrical input signal representing an acoustical signal from an input transducer of the hearing aid system;

splitting the input signal into a plurality of frequency bands;

forming a first group of frequency bands and a second group of frequency bands, wherein the first group of frequency bands comprises frequency bands that are interleaved with respect to frequency bands comprised in the second group of frequency bands;

alternating between selecting the first group of frequency bands or the second group of frequency bands;

processing the selected frequency bands in a first manner, hereby providing processed selected frequency bands;

processing the non-selected frequency bands in a second manner such that the non-selected frequency bands are attenuated relative to the selected frequency bands, hereby providing processed non-selected frequency bands;

providing an output signal based on the processed selected and non-selected frequency bands; and using the output signal to drive an output transducer of the hearing aid system.

In a specific variation of the disclosed embodiments and their variations the final method step of setting a gain or a hearing aid parameter or selecting a hearing aid feature may be omitted. Hereby a method of diagnosing an auditory neuro-synaptopathy results.

Generally the embodiments according to FIGS. 1-3 and their variations may be implemented based on a computer-readable storage medium having computer-executable instructions, which when executed carry out the methods disclosed with reference to FIGS. 1-3.

Generally any of the disclosed embodiments of the invention may be varied by including one or more of the variations disclosed above with reference to another of the disclosed embodiments of the invention. Thus the disclosed method embodiment may also be varied by including one or more of the hearing aid system variations.

According to still other variations, the present invention may be implemented for any audio device comprising an acoustical-electrical input transducer and an output transducer adapted to provide a perception of audio in a human being. Head sets, personal sound amplifiers and smart phones are examples of such audio devices.

The invention claimed is:

1. A method of fitting a hearing aid system comprising the steps of:
   providing a first test sound having a first intensity level and a first duration;
   providing a second test sound, having a second intensity level and a third duration;
   providing a period of silence, in between said first and second test sounds, wherein the period of silence has a second duration;
   prompting a person to detect the second test sound;
   receiving an input from the person in response to said prompting;
   determining the person's sensitivity to temporal masking based on the input from the person;
   identifying an auditory neuro-synaptopathy for the person if the sensitivity to temporal masking is increased compared to normal hearing persons; and
   setting a gain or a hearing aid parameter or selecting a hearing aid feature based on the result of said identification.

2. The method according to claim 1, wherein the magnitude of the first intensity level is sufficient to activate the medium spontaneous-rate nerve-fibres and/or the low spontaneous-rate nerve-fibres.

3. The method according to claim 1 comprising the further steps of:
   determining the duration of the period of silence that makes the second test sound just noticeable for the person; and
   determining that the sensitivity to temporal masking is increased relative to normal hearing persons if the determined duration of the period of silence is increased relative to the corresponding duration for normal hearing persons.

4. The method according to claim 1 comprising the further steps of:
   determining the level difference, between the first and the second intensity levels, that makes the second test sound just noticeable for the person; and
   determining that the sensitivity to temporal masking is increased relative to normal hearing persons if the determined level difference is decreased relative to the corresponding level difference for normal hearing persons.

5. The method according to claim 1, wherein the step of determining the person's sensitivity to temporal masking is carried out for a plurality of first intensity levels of the first test sound, and wherein the step of identifying an auditory neuro-synaptopathy for the person is carried out by determining that the sensitivity to temporal masking does not decrease for first intensity levels being sufficiently high to activate the medium spontaneous-rate nerve-fibres and/or the low spontaneous-rate nerve-fibres.

6. The method according to claim 1, wherein the first and second test sounds are selected from a group comprising: pure tones, warble tones and narrow-band noise.

7. The method according to claim 1, wherein the center frequency of the second test sound is frequency shifted relative to the center frequency of the first test sound, and wherein the frequency shift is less than 5% or less than 10% of the center frequency of the first test sound.

8. The method according to claim 3 wherein the step of determining the duration of the period of silence, that makes the second test sound just noticeable for the person comprises the step of:
   varying the duration of the period of silence until the second test sound is just noticeable for the person.

9. The method according to claim 4 wherein the step of determining the second intensity level, that makes the second test sound just noticeable for the person comprises the step of:
   varying the second intensity level until the second test sound is just noticeable for the person.

10. The method according to claim 1, wherein the step of selecting a hearing aid feature based on the result of said identification comprises selecting the hearing aid feature from a group of features comprising: frequency contrast enhancement and interleaved frequency band processing.

11. A non-transitory computer-readable medium storing instructions thereon, which when executed by a computer perform the following method:
   providing a first test sound having a first intensity level and a first duration;
   providing a second test sound, having a second intensity level and a third duration;
   providing a period of silence, in between said first and second test sounds, wherein the period of silence has a second duration;
   prompting a person to detect the second test sound;
   receiving an input from the person in response to said prompting;
   determining the person's sensitivity to temporal masking based on the input from the person;
   identifying an auditory neuro-synaptopathy for the person if the sensitivity to temporal masking is increased compared to normal hearing persons; and
   setting a gain or a hearing aid parameter or selecting a hearing aid feature based on the result of said identification.

12. A hearing test system comprising a computerized device having an electro-acoustical output transducer, a graphical user interface, a program storage for storing an executable program, and a processor for executing said program to perform the following method:
   providing a first test sound having a first intensity level and a first duration;
   providing a second test sound, having a second intensity level and a third duration;
   providing a period of silence, in between said first and second test sounds, wherein the period of silence has a second duration;
   prompting a person to detect the second test sound;
   receiving an input from the person in response to said prompting;
   determining the person's sensitivity to temporal masking based on the input from the person;
   identifying an auditory neurodegeneration for the person if the sensitivity to temporal masking is increased compared to normal hearing persons.

* * * * *